United States Patent
Birnbaum et al.

(10) Patent No.: US 6,405,077 B1
(45) Date of Patent: Jun. 11, 2002

(54) METHOD IN CONNECTION WITH PERSONAL NON-INVASIVE HEARTRATE MEASURING ARRANGEMENT WITH ALARM

(75) Inventors: Burton H. Birnbaum, Woodmere, NY (US); Pertti Puolakanaho, Oulu (FI)

(73) Assignee: Polar Electro Oy, Kempele (FI)

(*) Notice: Subject to any disclaimer, the term of this patent is extended or adjusted under 35 U.S.C. 154(b) by 0 days.

(21) Appl. No.: 09/232,895

(22) Filed: Jan. 15, 1999

(51) Int. Cl.[7] .............................................. A61B 5/024
(52) U.S. Cl. ...................................... 600/520; 128/905
(58) Field of Search .................................. 600/519, 520; 128/905, 903

(56) References Cited

U.S. PATENT DOCUMENTS

| | | | | |
|---|---|---|---|---|
| 4,788,983 A | * | 12/1988 | Brink et al. ................. | 128/734 |
| 5,007,430 A | * | 4/1991 | Dardik ......................... | 128/696 |
| 5,067,710 A | * | 11/1991 | Watterson et al. .......... | 272/129 |
| 5,323,784 A | * | 6/1994 | Shu .............................. | 128/707 |
| RE34,728 E | * | 9/1994 | Hall-Tipping ........... | 364/413.04 |
| 5,410,472 A | * | 4/1995 | Anderson ............... | 364/413.04 |
| 5,462,504 A | | 10/1995 | Trulaske et al. | |
| 5,464,012 A | * | 11/1995 | Falcone ....................... | 128/630 |
| 5,598,849 A | * | 2/1997 | Browne ....................... | 128/707 |
| 5,720,771 A | * | 2/1998 | Snell ............................ | 607/60 |
| 5,813,990 A | * | 9/1998 | Ryll ............................. | 600/500 |
| 5,853,351 A | | 12/1998 | Maruo et al. | |
| 6,163,718 A | * | 12/2000 | Fabrizio ....................... | 600/519 |

FOREIGN PATENT DOCUMENTS

| | | |
|---|---|---|
| DE | 3445654 A1 | 6/1986 |
| EP | WO 91/09374 | 6/1991 |
| EP | WO 98/44996 | 10/1998 |
| JP | 0 255 621 A1 | 2/1988 |

\* cited by examiner

*Primary Examiner*—Kennedy Schaetzle
(74) *Attorney, Agent, or Firm*—Hoffmann & Baron, LLP (57) ABSTRACT

The invention relates to a method applied in connection with a personal non-invasive heart rate measuring arrangement. In the method, information is supplied to the heart rate measuring arrangement to form several heart rate limit alarm pairs, each of which comprises a lower limit and an upper limit for the heart rate. Time information on each heart rate limit pair is also supplied in the method, the time information indicating a time period during which a heart rate limit alarm pair or at least one of the heart rate limits of a heart rate limit alarm pair is effective during the exercise, controlling the exercise. A heart rate limit alarm sequence progressing in accordance with the time information on the heart rate limit alarm pairs is formed in the method from the heart rate limit alarm pairs, and the heart rate limit alarm sequence is used during the exercise to control the exercise.

23 Claims, 7 Drawing Sheets

METHOD IN CONNECTION WITH PERSONAL NON-INVASIVE HEARTRATE MEASURING ARRANGEMENT WITH ALARM

BACKGROUND OF INVENTION

The invention relates to a heart rate monitor. The method is applied in a personal non-invasive heart rate measuring device. The heart rate measuring device can be, for example, a conventional two-part device comprising a usually belt-type heart rate transmitter containing EKG electrodes, and a wristband-type receiver unit in telemetric inductive or optical connection with the transmitter, the receiver unit comprising, for example, a microprocessor, a display and a user interface. Alternatively, the heart rate measuring device can be entirely integrated into a wristband, whereby a sensor, such as EKG electrodes or a pressure sensor, is also arranged in the wristband. Alternatively, all the components can also be integrated into a heart-rate-measuring belt. The sensor can also be an optical sensor measuring the heart rate.

Heart rate monitors comprise a heart rate limit alarm system to control the exercise performed by the user: the user is given an alarm if his/her heart rate during the exercise reaches or falls below the lower limit or reaches or exceeds the upper limit. The heart rate must be within a certain range in order for the exercise to be sufficiently efficient and yet not risky.

In currently known personal heart rate measuring devices, the heart rate limit alarms are implemented in such a way that a single pair of heart rate limits can be set in the device to control the exercise. This kind of heart rate limit alarm is rather limited, and it makes the exercise rather monotonous and too steady.

BRIEF DESCRIPTION OF INVENTION

The object of the invention is to provide a new method applied in connection with a personal non-invasive heart rate measuring arrangement, avoiding the problems and drawbacks associated with the known solutions.

In a first embodiment of the method information is supplied to the heart rate measuring arrangement to form several heart rate limit alarm pairs, each of which comprises a lower and an upper limit for the heart rate; and time information on each heart rate limit pair is also supplied in the method, the time information indicating a period of time during which a heart rate limit alarm pair or at least one of the heart rate limits of a heart rate limit alarm pair is effective during the exercise, controlling the exercise;

a heart rate limit alarm sequence progressing in accordance with the time information on the heart rate limit alarm pairs is formed from the heart rate limit alarm pairs; and the heart rate limit alarm sequence is used during the exercise to control the exercise.

In a second embodiment of the invention information is supplied to the heart rate measuring arrangement to form several heart rate limit alarm pairs, each of which comprises a lower and an upper limit for the heart rate; and time information on each heart rate limit pair is also supplied in the method, the time information indicating a period of time during which a heart rate limit alarm pair or at least one of the heart rate limits of a heart rate limit alarm pair is effective during the exercise, controlling the exercise;

one or more individual heart rate limits intended to fall within the time ranges between the time periods of the heart rate limit alarm pairs is supplied to the heart rate measuring arrangement;

a heart rate limit alarm sequence progressing in accordance with the time information on the heart rate limit alarm pairs and an instant of reaching one or more individual heart rate limits is formed from the heart rate limit alarm pairs and the one or more individual heart rate limits between the heart rate limit alarm pairs;

the heart rate limit alarm sequence is used during the exercise to control the exercise.

In a third embodiment of the invention information is supplied to the heart rate measuring arrangement to form several heart rate limit alarm pairs, each of which comprises a lower and an upper limit for the heart rate; and time information on each heart rate limit pair is also supplied in the method, the time information indicating a period of time during which a heart rate limit alarm pair or at least one of the heart rate limits of a heart rate limit alarm pair is effective during the exercise, controlling the exercise;

the lengths of one or more periods of change falling within one or more time ranges between the time periods of the heart rate limit alarm pairs are supplied to the heart rate measuring arrangement:

a heart rate limit alarm sequence progressing in accordance with the time information on the heart rate limit pairs and the supplied lengths of the one or more periods of change is formed from the heart rate limit alarm pairs;

the heart rate limit sequence is used during the exercise to control the exercise.

A fourth, fifth and sixth embodiment of the invention differ from the above three embodiments in respect of the time information supplied: the time information on each heart rate limit pair supplied in the method indicates a period of time during which the heart rate must be within the range of said heart rate limit alarm pair during the exercise.

The idea underlying the invention is to provide a heart rate limit sequence with multiple heart rate limits, the sequence comprising sections that control the exercise.

The advantage of the method of the invention is that it makes it possible to control the stress caused by the exercise in accordance with the situation and the fitness classification. It also enables the programming of interval type exercises in the device. The heart rate limit sequence of the invention can be programmed easily and quickly in the device, and if necessary, it can also be easily changed or replaced with another sequence. The trainer can give the trainee a long-term exercise sequence, but the trainee can also do it himself/herself. Also, training programs can be loaded in the heart rate monitor even from a long distance. For example, the Internet (WWW), a fixed telephone network or a mobile network can be used as a path for loading the exercise sequence. The preferred embodiments of the invention and the other embodiments that will be described in greater detail below enhance the advantages of the invention.

BRIEF DESCRIPTION OF FIGURES

The invention will now be described in greater detail by means of preferred embodiments, with reference to the attached drawings, in which.

DETAILED DESCRIPTION OF INVENTION

Figure 1:
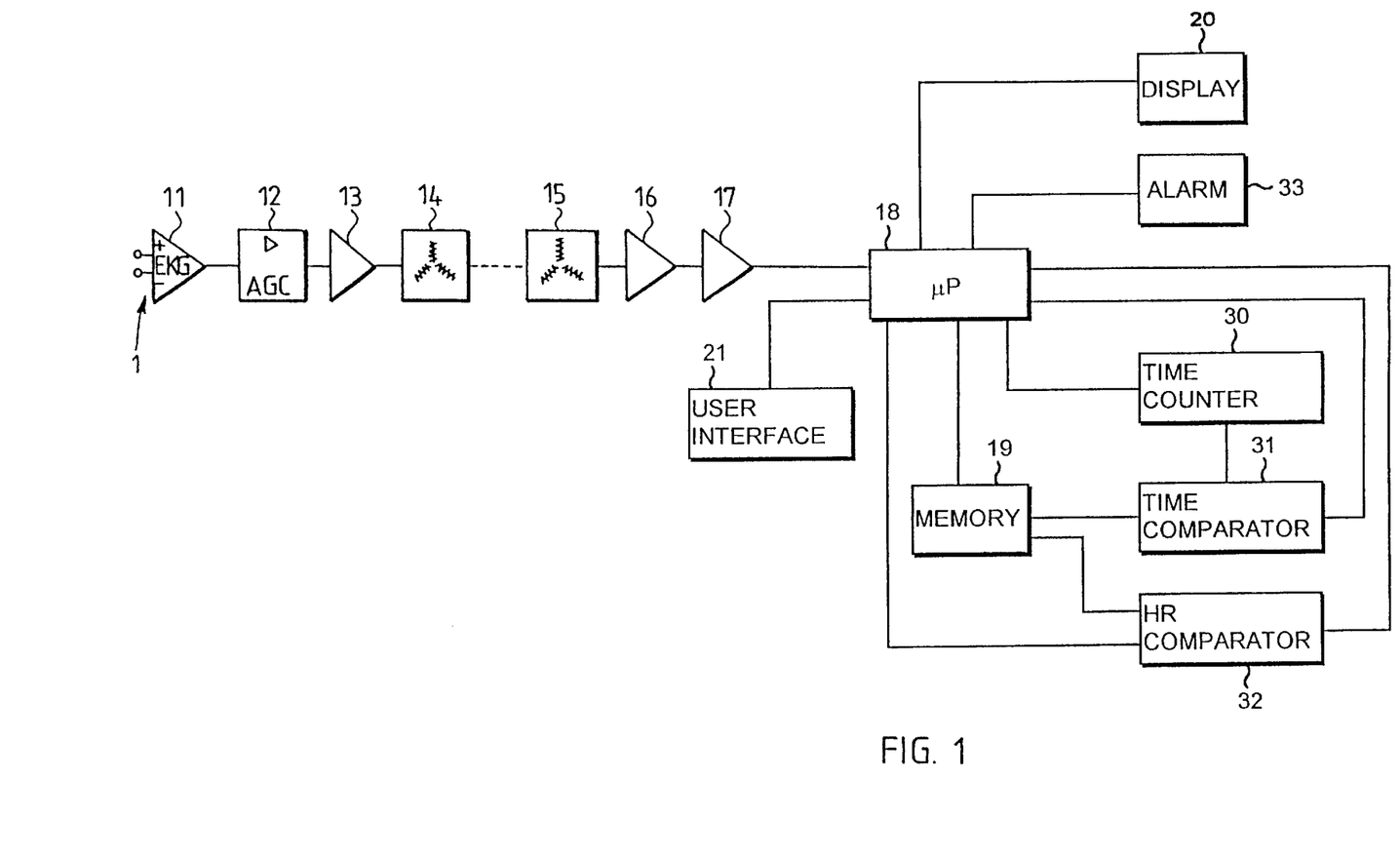
FIG. 1 is a block diagram of a telemetric heart rate measuring arrangement.

FIG. 1 is a telemetric heart rate measuring device, i.e. a heart rate measuring arrangement, which comprises electrodes 1; an EKG pre-amplifier 11 with differential input poles; an amplifier 12, such as an AGC amplifier; a power amplifier 13; a coil structure 14, 15; a pre-amplifier 16; a signal amplifier 17; a data processing unit 18, such as a microprocessor; a memory unit 19; and a display 20, such as a liquid crystal display. The electrodes of the telemetric heart rate measuring device in FIG. 1 are connected to the differential input poles of the EKG pre-amplifier. The heart rate signal given by the pre-amplifier 11 is amplified in the amplifier 12, for example in the AGC amplifier, which controls the power amplifier 13, and in the power amplifier is generated an AC or burst signal according to FIG. 2 to control the coils 14. The magnetic field detected by the receiver coils 15 is amplified in the pre-amplifier 16, from which the signal is supplied to the signal amplifier 17. The signal outputted from the signal amplifier 17 is processed in the data processing unit 18, which stores the heart rate data calculated in the measuring step in the memory unit 19 and shows it on the display 20. The receiver unit can also comprise a user interface 21, which may be, for example, a keyboard with one or more keys. The data processing unit 18 can be, for example, a microprocessor. The device also comprises components 30 to 33, which in particular pertain to the implementation of the operations of the invention, i.e. to the heart rate limit alarm sequence.

Components 1 to 14 form the measuring and transmitter unit A. Components 15 to 21 and 30 to 33 belong to the receiver unit B. The transmitter unit A and the receiver unit B may naturally also comprise other components. The measuring and transmitter unit A and the receiver unit B form the heart rate measuring arrangement.

Figure 2:
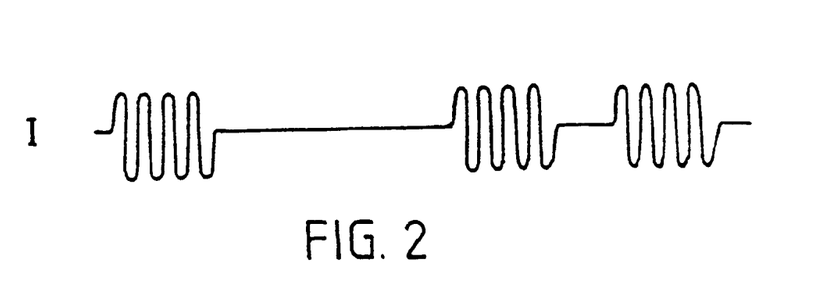
FIG. 2 shows a schematic view of a burst signal supplied to the magnetic coils of a transmitter unit.

In FIGS. 1 and 2, the transmitters A of the heart rate measuring devices typically transmit an about 5-kHz burst every time they detect an EKG signal. The transmission circuit of the transmitter unit A comprises a resonance circuit, which is activated by the heart rate. In the parallel resonance circuit, a capacitance is needed as well as the coil 14. The receiver unit B counts the heartbeat frequency, i.e. the heart rate, on the basis of the time difference of the signals transmitted in succession, i.e. on the basis of the time difference of the bursts. The data to be forwarded, i.e. the heart rate or heartbeat frequency, is thus contained in the transmission, encoded in the time between the groups of bursts.

Figure 3:
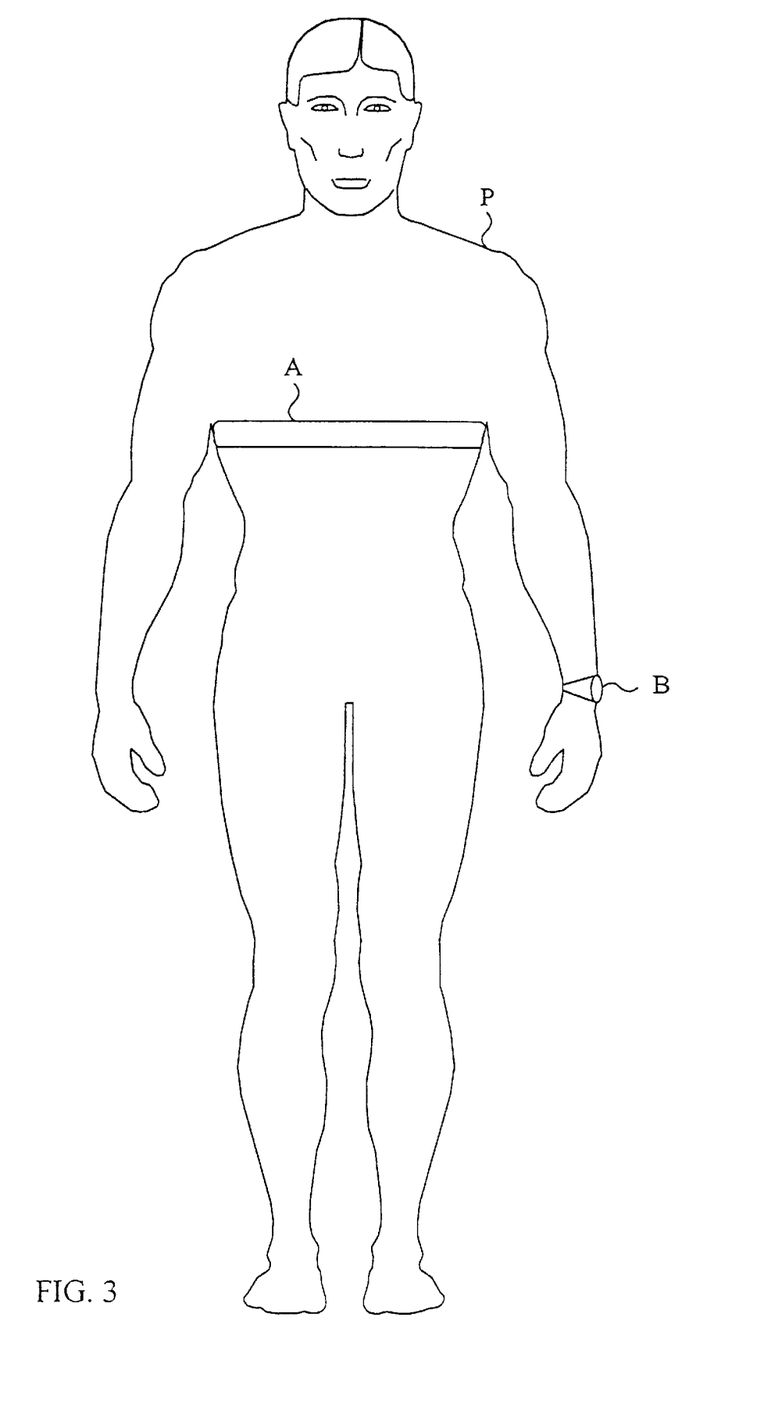
FIG. 3 shows a transmitter unit on a person's chest and a receiver unit on the person's wrist.

As shown in FIG. 3, the devices are usually such that the heart rate data measuring and transmitter unit A is attached around a person's P chest as a transmitter belt A, from which the measurement data is transmitted wirelessly by telemetry by means of the inductive circuit 14, 15 shown in FIG. 1 to the receiver unit B, which is often implemented as a wristband attached to a person's P wrist. Where cycling is concerned, the receiver unit B may be attached, for example, to the handlebar of the bicycle.

Figure 4:
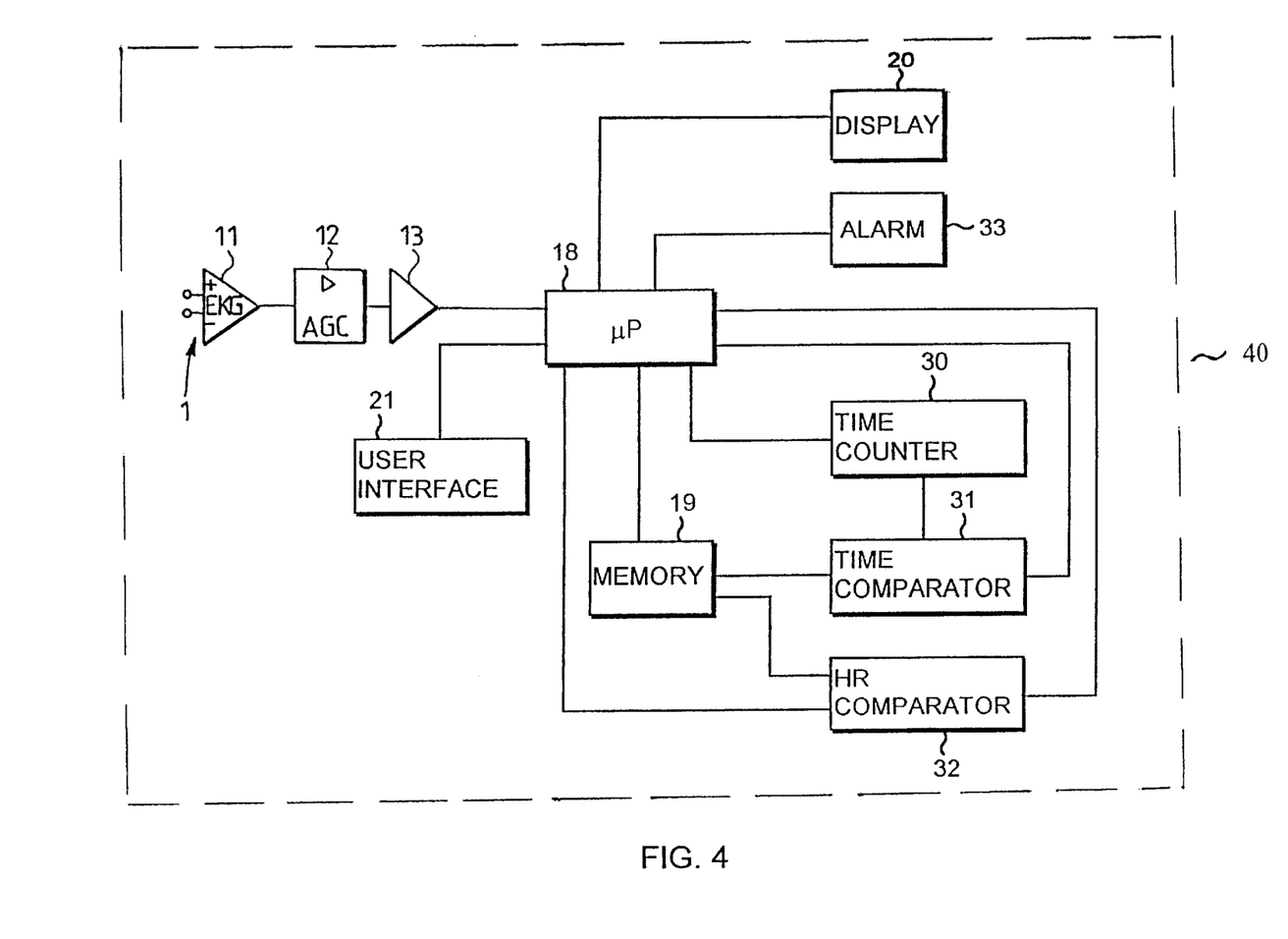
FIG. 4 shows a heart rate measuring arrangement integrated into a single unit.

In addition to the one-part device shown in FIG. 1, the implementation can also be as shown in FIG. 4, where a broken line 40 indicates that the components can be integrated into a single casing 40, for example into an electrode belt A or a wristband B. Solutions like this do not comprise separate transmitter and receiver units, since all components are integrated into a single unit, i.e. in practice the electrodes are integrated into the same unit as the data processing unit. Naturally, neither the coils 14 and 15 nor all the amplifiers 13, 16, 17 of FIG. 1 are needed in these solutions. The device of FIG. 4 comprises components 1 to 13, 18 to 21, and 30 to 33.

FIG. 1 also shows an external means for supplying data, such as a microprocessor 45, and a supply means 46 connected thereto. Via the supply means, information on the heart rate limits can be supplied to unit B of the heart rate measuring arrangement. The connection can be an inductive magnetic connection between the supply means 46 and the coil 15. Such an inductive magnetic connection would be similar to the connection used for transferring heart rate information between the coils 14, 15. Another alternative would be an optical connection, where the coil 15 would be replaced with or supplemented with an optical receiver and the supply means 46 would be provided with an optical transmitter.

Figure 5:
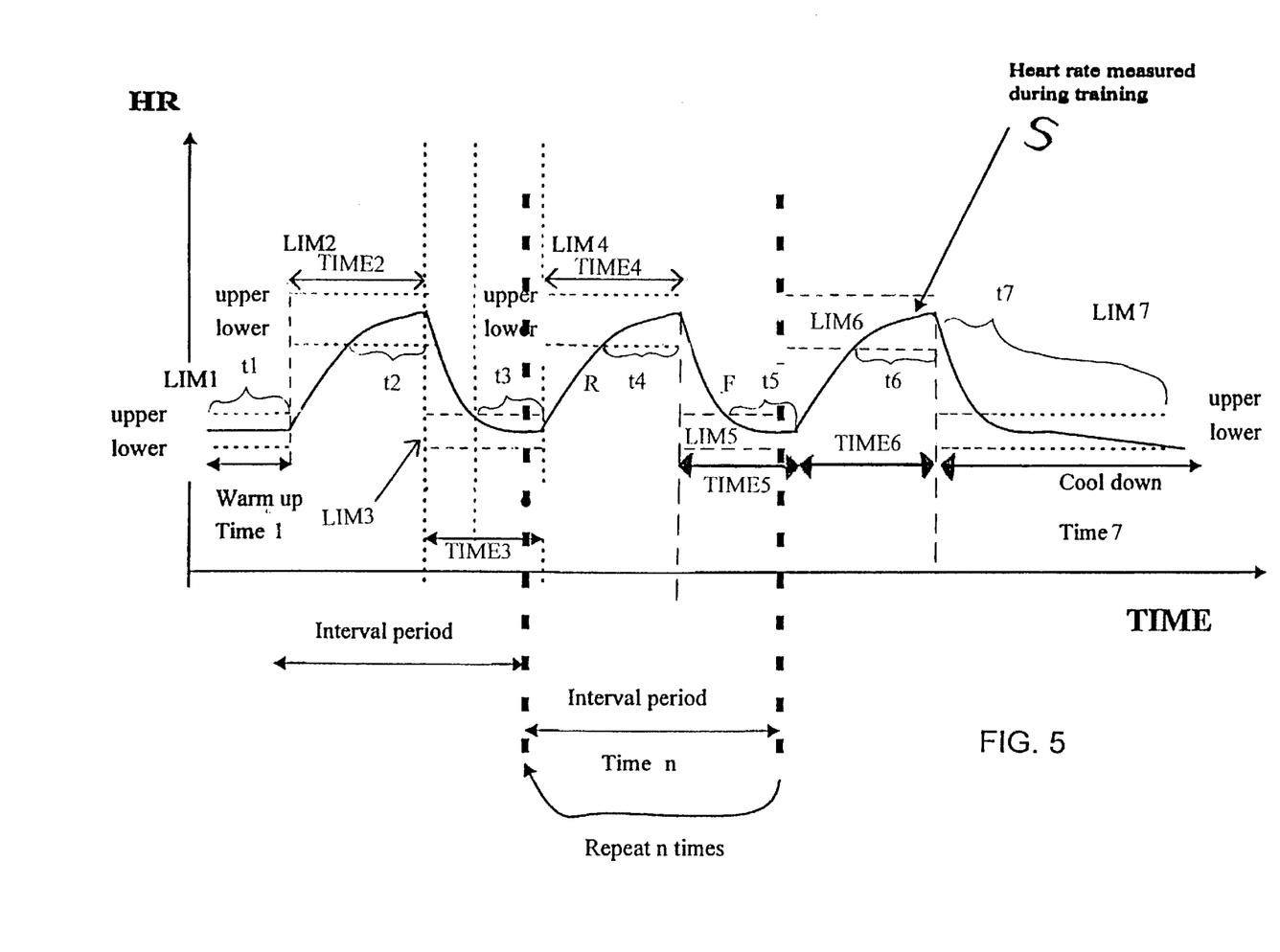
FIG. 5 illustrates a first preferred embodiment of the method with successive heart rate limit alarm pairs.
Figure 6:
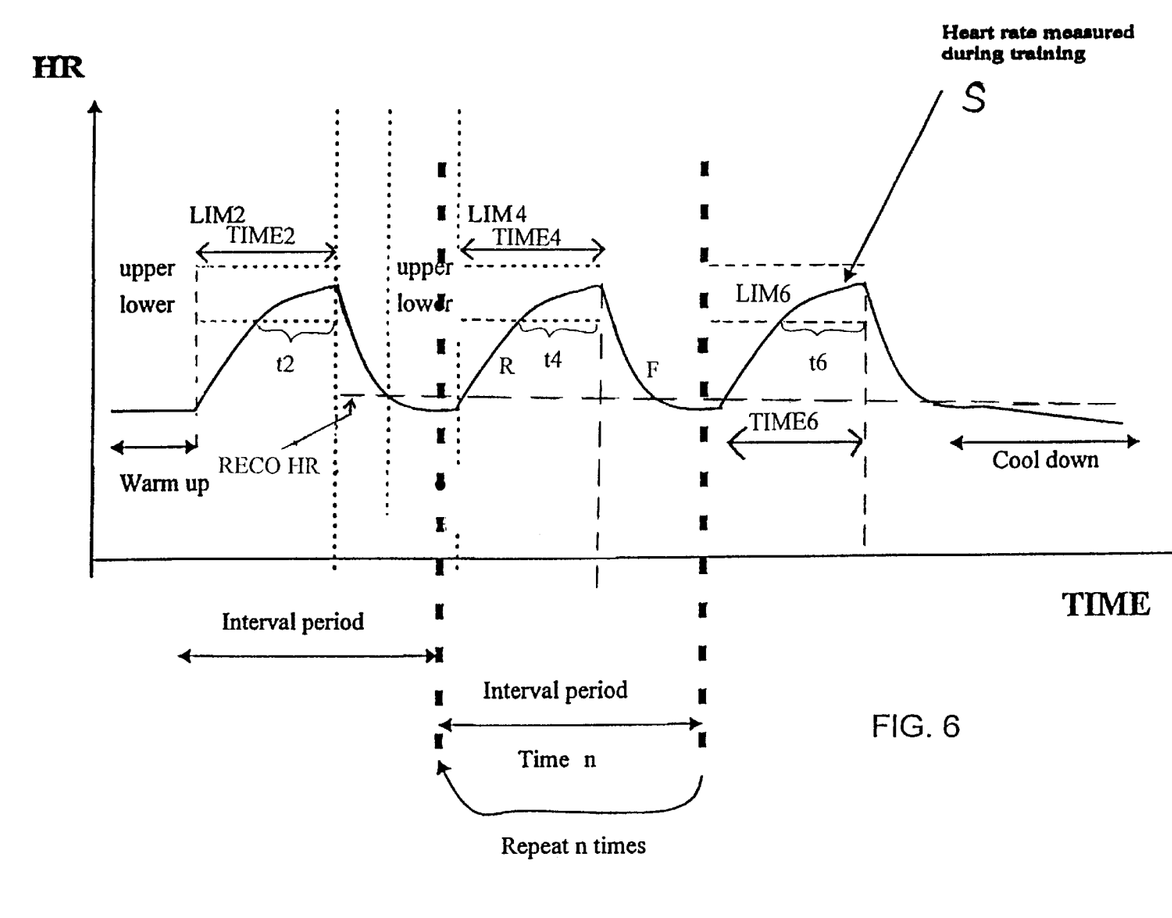
FIG. 6 illustrates a second preferred embodiment of the method, in which there is an individual heart rate limit for recovery between the heart rate limit alarm pairs.
Figure 7:
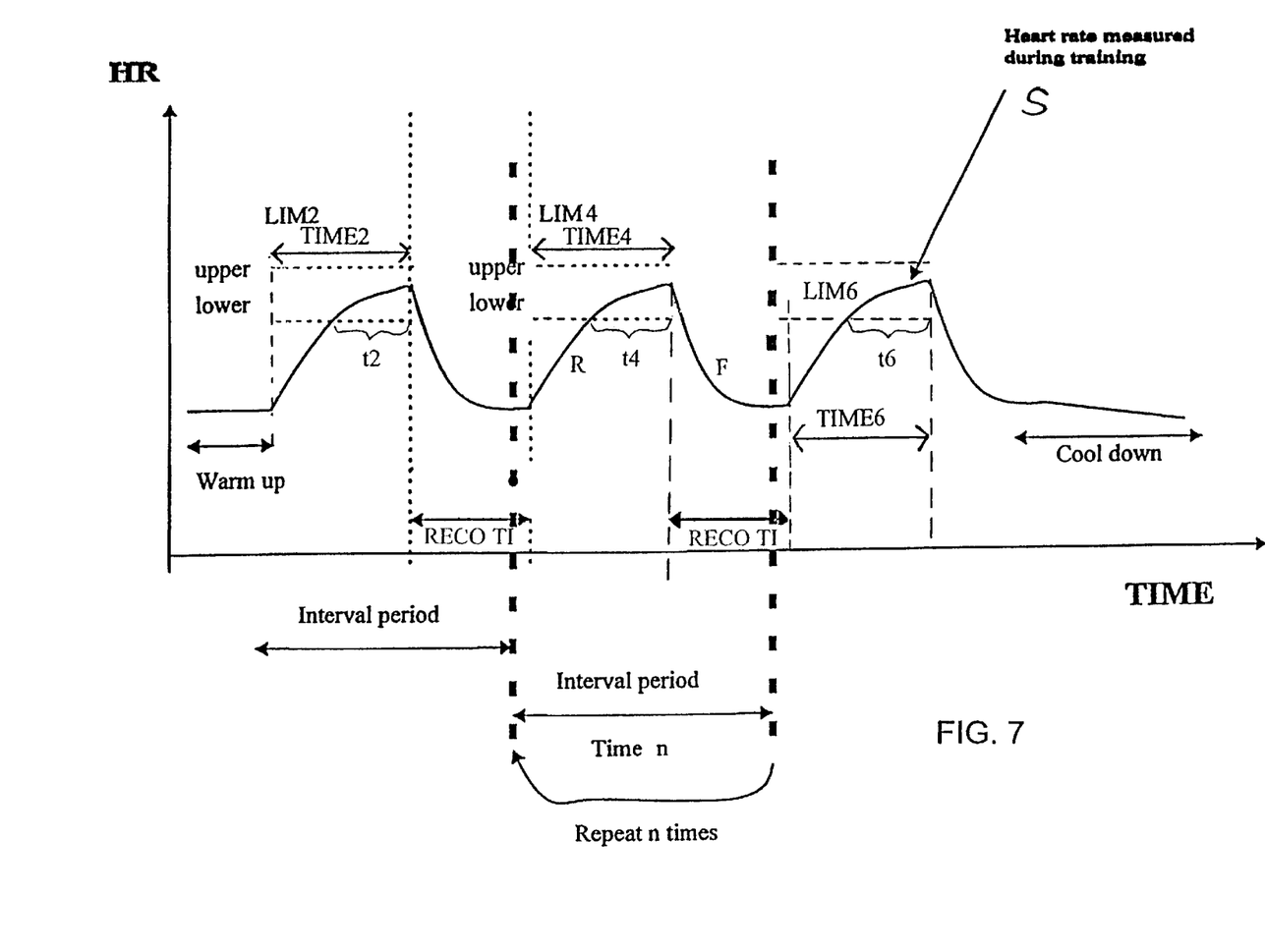
FIG. 7 illustrates a third preferred embodiment of the method, in which there is a period of change relating to recovery between the heart rate limit alarm pairs.

Three different types of heart rate limit alarm sequences are shown in FIGS. 5 to 7. The heart rate limit pairs are indicated by LIM1 to LIM7, and the information on their effectiveness is indicated by TIME1 to TIME7. The lower limits for the heart rate in the heart rate limit pairs are indicated by 'lower', and the upper limits by 'upper'. The difference between the heart rate limit alarm sequences of FIGS. 5 to 7 principally pertains to the detection of sufficient recovery after a high heart rate limit, for example LIM2, so that the next high heart rate limit pair LIM4 can be activated to control the exercise.

With regard to the heart rate measuring arrangement, the most important parts of the invention are blocks 18–19, 21 and 30–33, which pertain to the use of heart rate limits LIM and associated time information TIME for controlling the exercise using the heart rate limit alarm sequence.

With regard to the formation and use of the heart rate limit alarm sequence controlling the exercise the following needs to be stated. Apart from the microprocessor (or other such data processing means) 18, the memory 19 and the user interface 21, the heart rate alarm arrangement also comprises a time counter 30, a time comparator 31, and a heart rate comparator 32. Information on the values (upper, lower) of the heart rate limit pairs (LIM), on the values of individual recovery heart rate limits between the heart rate limit pairs (recovery heart rate, RECO HR) and on the recovery times (RECO TI) are supplied via the user interface 21 to the microprocessor 18, or at least the supply is controlled by the microprocessor 18. The information supplied is forwarded from the microprocessor, or controlled by the microprocessor, to the memory 19, with which the microprocessor 18 is connected. The heart rate measuring arrangement comprises a heart rate limit alarm (block 33).

Information is supplied from the memory 19 to the heart rate comparator 32, the information comprising information on the heart rate limit pairs LIM (FIGS. 5 to 7) and individual heart rate limits RECO HR (FIG. 6). The measured heart rate HR is also supplied from the microprocessor 18 to the heart rate comparator. Information is also supplied from the memory 19 to the time comparator 31, which receives information on the TIME (FIGS. 5 to 7) and RECO TI (FIG. 7). The time comparator 31 also receives a control signal from the time counter 30, which is controlled by the microprocessor 18.

The heart rate comparator 32 compares the measured heart rate with the heart rate limit pair LIM (FIGS. 5 to 7) or the individual heart rate limit RECO HR in the heart rate limit alarm sequence. The output of the heart rate comparator 32 and the output of the time comparator 31 are connected with the microprocessor 18, which decides whether the situation is such that an alarm needs to be given. In other words, the microprocessor checks whether the current heart rate measured during the exercise is outside the range defined by the lower limit 'lower' and the upper limit 'upper' of the heart rate limit alarm pair, such as LIM2. On the basis of the information obtained from the time comparator 31 the microprocessor knows the instant when the heart rate limit pair changes (FIG. 5). On the basis of the information obtained from the time comparator, the microprocessor knows when the effect of the heart rate limit pair, for example LIM2, LIM4 or LIM6, ends so that the exercise will have to be controlled on the basis of an individual heart rate limit RECO HR (FIG. 6) or the period of change RECO TI (FIG. 7).

If the reaching of an individual lower heart rate limit RECO HR between the heart rate limit alarm pairs, such as LIM2, LIM4, as in FIG. 6, is monitored, then the information obtained from the heart rate comparator 32 tells the microprocessor 18 whether that part of the sequence has been reached where the next heart rate limit pair LIM4 must be set to control the exercise.

If the ending of the period of change RECO TI between the heart rate limit alarm pairs, such as LIM2, LIM4, as in FIG. 7, is monitored, then the information obtained from the time comparator 31 tells the microprocessor 18 whether that part of the sequence has been reached where the next heart rate limit pair LIM4 must be set to control the exercise.

Curve S in FIGS. 5 to 7 represents the heart rate HR during the exercise, measured by the heart rate measuring arrangement. The heart rate is shown on the vertical axis in the figures.

FIG. 5 illustrates a first embodiment of the method of the invention, in which the heart rate limit alarm sequence comprises successive heart rate limit pairs. The method is applicable in a personal non-invasive heart rate measuring arrangement. In the first embodiment, information is supplied from the user interface 21 to the heart rate measuring arrangement to form several heart rate limit alarm pairs LIMI to LIM7. Each heart rate limit pair comprises a lower limit ('lower') and an upper limit ('upper') for the heart rate. Time information TIME1 ... 7 on each heart rate limit pair is also supplied in the method, the information indicating a time period during which a heart rate limit alarm pair or at least one of the heart rate limits of a heart rate limit alarm pair (the lower limit on the way up, and the upper limit on the way down) is effective during the exercise, controlling the exercise. A heart rate limit alarm sequence progressing in accordance with the time information on the heart rate limit alarm pairs is formed from the heart rate limit alarm pairs and subsequently used during the exercise to control the exercise. FIG. 5 shows four heart rate limit pairs LIM1, LIM3, LIM5 and LIM7 with a low heart rate value, and three heart rate limit pairs LIM2, LIM4 and LIM6 with a higher heart rate value.

In a preferred embodiment the heart rate limit pairs LIM1, LIM3, LIM5 and LIM7 with a lower heart rate value are identical in respect of the lower limits and the upper limits, so with regard to these lower heart rate limit pairs it is sufficient that the value of the heart rate limit pair is supplied once. The heart rate limit pairs LIM2, LIM4 and LIM6 with a higher heart rate value are here also mutually identical in respect of the lower limits and the upper limits, so with regard to these upper heart rate limit pairs it is also sufficient that the value of the heart rate limit pair is supplied once.

The lower heart rate limit pairs LIM1, LIM3, LIM5 and LIM7 in the figure are, for example, within the heart rate range 110 to 130 bpm (beats per minute). The higher heart rate limit pairs LIM2, LIM4 and LIM6 are, for example, within the heart rate range 150 to 180 bpm.

With regard to the higher heart rate limit pairs LIM2, LIM4 and LIM6 it is important that the time information indicating how long the heart rate HR during the exercise should preferably stay within the range between the lower and the upper limits of the heart rate limit alarm pair has also been supplied to the heart rate measuring arrangement. In the method, a sound or other alarm is given during the exercise if the heart rate measured is below the lower limit of the high heart rate limit pairs LIM2, LIM4 and LIM6 or above their upper limit. With regard to the heart rate limit pairs LIMI, LIM3, LIM5 and LIM7 within the lower heart rate range, it is not necessary to give the time information, at least not with regard to the two middle heart rate limit pairs LIM3, LIM5, and it is also not always necessary, nor even sensible, to give a heart rate limit alarm, since the actual meaning of the two middle heart rate limit pairs LIM3, LIM5 of the lower heart rate limit pairs is to monitor that the heart rate is restored to a sufficiently low value so that it is possible to set the next higher heart rate limit pair, for example LIM4 or LIM6, as a target in the sequence.

The first heart rate limit pair LIM1 in FIG. 5 concerns the warm-up part of the exercise, and the last heart rate limit pair LIM7 concerns the cool-down at the end of the exercise. The heart rate limit pairs for the warm up and the cool down and any associated time information are not so necessary as the higher heart rate limit pairs LIM2, LIM4 and LIM6 of the sequence, which are the targets aimed at when the heart rate is raised in the exercise.

FIG. 5 shows first a warm-up period controlled by heart rate limit pair LIM1 for a time TIME1 defined for it. The time period changes to TIME2, and the exercise will now be controlled by heart rate alarm limit pair LIM2. In practice this means that at first an alarm 33 supplies a signal that tells the user that the heart rate HR measured is too low, and the alarm continues until the user's heart rate HR rises to the range between the lower limit and the upper limit of the heart rate limit alarm pair LIM2. If the device is programmed such that an alarm is also given during the recovery as the heart rate is falling from a higher heart rate limit pair, such as LIM2, toward a lower heart rate limit pair, such as LIM3, then the device gives an alarm when time period TIME3 begins and the alarm continues until the heart rate HR is within the range of heart rate limit alarm pair LIM3. The sequence progresses in a similar way controlled by the next heart rate limit pairs LIM4 to LIM7 and their time periods TIME4 to TIME7 until the sequence comes to an end, i.e. until the end of the cool-down period.

FIG. 6 illustrates a second preferred embodiment of the method, in which there is an individual recovery heart rate limit RECO HR between the heart rate limit pairs.

The difference between FIG. 6 and FIG. 5 is that in FIG. 6 there is only an individual low heart rate limit RECO HR between each two high heart rate limit pairs LIM2, LIM4, LIM6 and not a heart rate limit pair (LIM3, LIM5) like in FIG. 5. In the embodiment of FIG. 6, information is thus supplied to the heart rate measuring arrangement to form several heart rate limit alarm pairs LIM2, LIM4, LIM6, each of which comprises a lower and an upper limit for the heart rate. In practice the pairs are higher heart rate limit pairs LIM2, LIM4 and LIM6. Time information TIME2, TIME4, TIME6 on each supplied heart rate limit pair LIM2, LIM4 and LIM6 is also supplied in the method, the information indicating a time period during which the corresponding heart rate limit alarm pair or at least one of the heart rate limits of the heart rate limit alarm pair is effective during the exercise, controlling the exercise. The method of the second embodiment illustrated in FIG. 6 differs from that of the first embodiment illustrated in FIG. 5 in that one or more individual heart rate limits intended to fall within the time ranges between the time periods of the heart rate limit alarm pairs LIM2, LIM4, LIM6 are supplied to the heart rate measuring arrangement, the limit in practice being the recovery limit RECO HR indicating that the heart rate is being restored to a lower value, the limit in FIG. 6 being shown after the first heart rate limit pair LIM2. In the method, a heart rate limit alarm sequence progressing in accordance with the time information on the heart rate limit alarm pairs and an instant of reaching one or more individual heart rate limits RECO HR is formed from the heart rate limit alarm pairs and the one or more individual heart rate limits RECO HR between the heart rate limit alarm pairs and subsequently used to control the exercise. There are or can be similar recovery heart rate limits RECO HR after the second heart rate limit pair LIM4 and the third heart rate limit pair LIM6.

FIG. 7 illustrates a third preferred embodiment of the method, in which there is a period of change relating to recovery RECO TI between the heart rate limit pairs, such as heart rate limit pairs LIM2 and LIM4, or pairs LIM4 and LIM6. In other words, unlike in the second embodiment illustrated in FIG. 6, the heart rate is considered to have been restored sufficiently in FIG. 7 when the period of change RECO TI (recovery time) comes to an end. A similar recovery time RECO TI can also be imagined after the other two high heart rate limit pairs LIM4 and LIM6. In the method, information is supplied to the heart rate measuring arrangement to form several (at least two) heart rate limit alarm pairs LIM2, LIM4, LIM6, each of which comprises a lower and an upper limit for the heart rate. Time information TIME2, TIME4, TIME6 on each heart rate limit pair is also supplied in the method, the information indicating a time period during which a heart rate limit alarm pair or at least one of the heart rate limits of a heart rate limit alarm pair is effective during the exercise, controlling the exercise. The third embodiment illustrated in FIG. 7 differs from the first or second embodiments in that the lengths of the one or more periods of change RECO TI falling within the one or more time ranges between the time periods of the heart rate limit alarm pairs are supplied to the sequence to the heart rate measuring arrangement. A heart rate limit alarm sequence progressing in accordance with the time information TIME2, TIME4, TIME6 on the heart rate limit pairs and the supplied lengths of the one or more periods of change RECO TI is formed from the heart rate limit alarm pairs LIM2, LIM4, LIM6 and subsequently used to control the exercise.

With regard to each of the three embodiments, it has already been stated that a heart rate limit alarm pair or at least one of the heart rate limits of a heart rate limit alarm pair is effective during the exercise, controlling the exercise. If only the first part of the above definition (i.e. the heart rate limit alarm pair) is taken into account, i.e. if it is a heart rate limit alarm pair as a pair that is effective during the exercise, controlling the exercise, then it is evident that as the heart rate rises, the upper limit of a heart rate limit pair such as LIM2 is not relevant until the lower limit has been exceeded. The invention should thus be understood such that a given heart rate limit pair is effective as a pair, but the upper limit of the pair is not necessarily activated until the lower limit has been exceeded. With reference to FIG. 5, it is equally evident that, for example, as the heart rate falls, the lower limit of a heart rate limit pair such as LIM3 is not relevant until the heart rate has fallen below the upper limit. As the heart rate falls, the invention should be understood such that a given heart rate limit pair is effective as a pair, but the lower limit of the pair is not necessarily activated until the heart rate has fallen below the upper limit. In other words, either both the upper and the lower limit of the heart rate limit alarm pair are actively effective for the full duration of a time period indicated by the time information on the heart rate limit pair during the exercise, controlling the exercise, or when the heart rate measured by the heart rate measuring arrangement has changed to the range between the heart rate limits of a heart rate limit alarm pair, both the heart rate limits of the heart rate limit alarm pair are actively effective during a time period indicated by the time information on the heart rate limit pair during the exercise, controlling the exercise.

With reference to the above, it is pointed out that the time information TIME1 to TIME7 in FIGS. 5 to 7 is presented such that each time period TIMEI to TIME7 also comprises the initial time needed to reach the first heart rate limit of the heart rate limit pair. In other words, the time information TIME1 to TIME7 in FIGS. 5 to 7 is presented in principle such that each time period TIME1 to TIME7 contains not only the time the heart rate is within the heart rate limit pair but also the time preceding the time concerned, i.e. the time needed by the heart rate to reach the range concerned, i.e. to rise or fall. In each of the first three embodiments time information on each heart rate limit pair is supplied in the method, the information indicating a time period during which a heart rate limit alarm pair or at least one of the heart rate limits of a heart rate limit pair is effective during the exercise, controlling the exercise.

Differently from the above, in the fourth, fifth and sixth embodiments of the invention the time information on each heart rate limit pair supplied in the method indicates a time period during which the heart rate must be within the range of said heart rate limit alarm pair during the exercise. In the fourth, fifth and sixth embodiments the time information supplied is thus the time that the heart rate must be within the range. These time periods are indicated by t1 to t7 in FIGS. 5 to 7, and they are shorter than time periods TIME1 to TIME7.

In a preferred embodiment of the invention, the method is such that the heart rate limit alarm sequence controlling the exercise comprises a section where the heart rate rises R and a section where the heart rate falls F, the sections together forming an interval period in the heart rate limit alarm sequence.

In a preferred embodiment, the number of the interval sequences is supplied to the heart rate measuring arrangement, and a corresponding number of successive interval periods is formed in the heart rate limit alarm sequence. The sequence is thus quick to supply and form, and repeated sections occur in the sequence. In FIGS. 5 to 7 there are three successive interval periods. The number of the interval periods can be set as desired.

The first embodiment illustrated in FIG. 5 shows an interval period where the section where the heart rate rises is between a lower heart rate limit pair LIM3 and the next higher heart rate limit pair LIM4 in the heart rate limit alarm sequence, and the section where the heart rate falls is between said higher heart rate limit pair LIM4 and the next lower heart rate limit pair LIM5.

The second embodiment illustrated in FIG. 6 shows an interval period where the section where the heart rate rises is between an individual low heart rate limit and the next higher heart rate limit pair in the heart rate limit alarm sequence, and the section where the heart rate falls is between said higher heart rate limit pair and the next individual lower heart rate limit.

The third embodiment of the invention illustrated in FIG. 7 shows an interval period where the section where the heart rate rises is between the end point of the period of change and the next higher heart rate limit pair, and the section where the heart rate falls is the next period of change.

From the user's point of view, a good embodiment is one in which the information supplied in order to form heart rate limits and heart rate limit pairs is information directly indicating the heart rate limit values. For example, the user sets values 100 and 130 for the heart rate limit pairs to be used as the lower heart rate limit pairs, and values 150 and 180 for use as the higher heart rate limit pairs.

The same also applies to the supply of time information TIME1, TIME2, . . . and individual heart rate limits RECO HR and periods of change RECO TI, i.e. they are supplied directly as actual values, for example such that the recovery heart rate limit indicating the recovery of the user's heart rate in FIG. 6 is supplied directly as 115 bpm, and the period of change RECO HR is supplied as minutes or seconds.

The information supplied in order to form heart rate limits and heart rate limit pairs may also be indirect auxiliary information, which is used by the heart rate measuring arrangement to calculate the direct values of the heart rate limits and heart rate limit pairs used for the heart rate limit alarm sequence. The auxiliary information can be, for example, a percentage or some other proportion of the maximum heart rate or oxygen intake. A prerequisite is that a calculation formula is stored in the heart rate monitor.

A third alternative is that the information supplied to form heart rate limits and heart rate limit pairs is measurement information measured by the heart rate measuring arrangement and used by it to calculate the heart rate limit values. In addition, auxiliary information can be supplied. The measurement information is, for example, the maximum heart rate measured and the heart rate at rest. The auxiliary information can be, for example, the person's age, weight or some other such factor. Also here a prerequisite is that a calculation formula is stored in the heart rate monitor.

With reference to block 33 it is pointed out that to control the exercise, the heart rate measuring arrangement gives the person an alarm. The alarm continues until the person's measured heart rate is within the range between the lower and upper heart rate limits of a heart rate limit alarm pair, such as LIM2. If, on the other hand, the heart rate is within the correct range, then an alarm is given if the person's measured heart rate rises above or falls below the range defined by the lower and upper heart rate limits of the heart rate limit alarm pair, such as LIM2.

Alarms are thus used to help the person affect the stress caused by the exercise and thereby change the heart rate in a desired direction, or in the opposite case to keep the heart rate within the desired range.

It will be obvious to those skilled in the art that as technology advances, the basic idea of the invention can be implemented in many different ways. The invention and its embodiments are thus not limited to the above examples but can vary within the scope of the claims.

What is claimed is:

1. A method applied in connection with a personal non-invasive heart rate measuring arrangement, comprising:
   supplying information to the heart rate measuring arrangement to form several heart rate limit alarm pairs, each of which comprises a lower heart rate limit and an upper heart rate limit,
   supplying time information on each heart rate limit pair to the heart rate measuring arrangement, the time information indicating a time period during which a heart rate limit alarm pair or at least one of the heart rate limits of a heart rate limit alarm pair is effective during an exercise,
   forming a heart rate limit alarm sequence progressing in accordance with the time information on the heart rate limit alarm pairs,
   using the heart rate limit alarm sequence during the exercise to control the exercise, the heart rate limit alarm sequence controlling the exercise comprising a section where the heart rate rises and a section where the heart rate falls, the sections together forming an interval period in the heart rate limit alarm sequence,
   supplying the number of said interval periods to the heart rate measuring arrangement wherein a number of successive interval periods is formed in the heart rate limit alarm sequence.

2. A method as claimed in claim 1, wherein the section of the interval period where the heart rate rises is between a lower heart rate limit pair and the next higher heart rate limit pair in the heart rate limit alarm sequence, and the section where the heart rate falls is between said higher heart rate limit pair and the next lower heart rate limit pair.

3. A method as claimed in claim 1, further comprising the step of activating both heart rate limits of a heart rate limit alarm pair for the full duration of a time period indicated by the time information on the heart rate limit pair.

4. A method as claimed in claim 1, further comprising the step of activating both heart rate limits of a heart rate alarm pair during a time period indicated by the time information on the heart rate limit pair when the heart rate measured by the heart rate measuring arrangement has changed such that it is within the range defined by the heart rate limits of a heart rate limit alarm pair.

5. A method as claimed in claim 1, wherein the information supplied to form the heart rate limits and heart rate limit pairs is information directly indicating the heart rate limit values.

6. A method as claimed in claim 1, further comprising the step of supplying the heart rate limit pairs and the associated time information and any other information to be supplied to the heart rate measuring arrangement via a wireless receiver unit contained in the heart rate measuring arrangement.

7. A method as claimed in claim 6, further comprising the step of supplying the heart rate limit pairs and the associated time information and any other information to be supplied to the heart rate measuring arrangement wirelessly to the heart rate measuring arrangement via an inductive receiver unit contained in the heart rate measuring arrangement, the receiver unit receiving information from an information inputting unit which is wirelessly connected with the heart rate measuring arrangement.

8. A method as claimed in claim 6, further comprising the step of supplying the heart rate limit pairs and the associated time information and any other information to be supplied to the heart rate measuring arrangement to the heart rate measuring arrangement via an optical receiver unit contained in the heart rate measuring arrangement, the receiver unit receiving information from the information inputting unit which is wirelessly connected with the heart rate measuring arrangement.

9. A method as claimed in claim 1, further comprising the step of providing an alarm to a person performing the exercise whereby the person can control the exercise.

10. A method as claimed in claim 9, further comprising the step of continuing the alarm until the person's measured heart rate is within the range between the heart rate limits of a heart rate limit alarm pair.

11. A method as claimed in claim 9, further comprising the step of providing the alarm if the person's measured heart rate rises above or falls below the range defined by the heart rate limits of a heart rate limit alarm pair.

12. A method applied in connection with a personal non-invasive heart rate measuring arrangement, comprising:
  supplying information to the heart rate measuring arrangement to form several heart rate limit alarm pairs, each of which comprises a lower heart rate limit and an upper heart rate limit,
  supplying time information on each heart rate limit pair to the heart rate measuring arrangement, the time information indicating a time period during which the heart rate must be within the range of said heart rate limit alarm pair during the exercise;
  forming a heart rate limit alarm sequence progressing in accordance with the time information on the heart rate limit alarm pairs,
  using the heart rate limit alarm sequence during the exercise to control the exercise, the heart rate limit alarm sequence controlling the exercise comprising a section where the heart rate rises and a section where the heart rate falls, the sections together forming an interval period in the heart rate limit alarm sequence,
  supplying the number of said interval periods to the heart rate measuring arrangement wherein a number of successive interval periods is formed in the heart rate limit alarm sequence.

13. A method for controlling an exercise performed by a person, comprising:
  providing a heart rate measuring arrangement capable of monitoring a current heart rate of said person during said exercise;
  programming said arrangement with a predetermined heart rate limit alarm sequence, said sequence including at least two successive interval periods, each of said interval periods including a first section wherein said current heart rate is rising and a second section wherein said current heart rate is falling, each of said first sections including a heart rate limit alarm pair, said heart rate limit alarm pair including a lower heart rate limit and an upper heart rate limit, and wherein said sequence further includes time information, said time information providing an operating time period for the heart rate limit alarm pair in each of said successive intervals;
  operating said arrangement in accordance with said predetermined heart rate limit alarm sequence during said exercise whereby said current heart rate is monitored over the length of said sequence and wherein said current heart rate is compared to said heart rate limit alarm pair as said sequence moves through each successive interval; and
  providing feedback to said person based on the comparison of said current heart rate to said heart rate limit alarm pair.

14. The method according to claim 13, wherein each of said second sections includes a heart rate limit alarm pair, said heart rate limit alarm pair of said second section including a lower heart rate limit and an upper heart rate limit, said lower and upper heart rate limits of said heart rate limit alarm pair of said second section being less than said lower and upper heart rate limits of said heart rate limit alarm pair of said first section, respectively.

15. The method according to claim 13, wherein each of said second sections includes an individual heart rate limit, said individual heart rate limit of said second section being less than said lower heart rate limit of said heart rate limit alarm pair of said first section.

16. The method according to claim 13, wherein both said lower heart rate limit and said upper heart rate limit of said heart rate limit alarm pair of said first section are actively affective for the full duration of said time period established by said time information.

17. The method according to claim 13, wherein the values of said lower and upper heart rate limits are fixed values.

18. The method according to claim 13, wherein said heart rate measuring arrangement includes a wireless receiver unit, and wherein said programming step is accomplished via transfer of data to said wireless receiver unit.

19. The method according to claim 13, wherein said heart rate measuring arrangement includes an inductive receiver unit and an information inputting unit, and wherein said programming step is accomplished via wireless transfer of data to said inductive receiver unit; and
  wherein said receiver unit receives information from said information inputting unit, said information inputting unit being wirelessly connected to said heart rate measuring arrangement.

20. The method according to claim 13, wherein said heart rate measuring arrangement includes an optical receiver unit and an information inputting unit, and wherein said programming step is accomplished via wireless transfer of data to said optical receiver unit; and
  wherein said receiver unit receives information from said information inputting unit, said information inputting unit being wirelessly connected to said heart rate measuring arrangement.

21. The method according to claim 13, wherein said heart rate measuring arrangement further includes an alarm for providing the feedback to said person.

22. The method according to claim 21, wherein said alarm is activated until said person's current heart rate is between said lower heart rate limit and said upper heart rate limit of the active heart rate limit alarm pair.

23. The method according to claim 21, wherein said alarm is activated if said person's current heart rate rises above said upper heart rate limit or falls below said lower heart rate limit of the active heart rate limit alarm pair.

* * * * *